United States Patent
Ng et al.

(10) Patent No.: US 6,454,714 B1
(45) Date of Patent: Sep. 24, 2002

(54) ULTRASONIC HARMONIC FLASH SUPPRESSION

(75) Inventors: Gary Ng, Bothell; James R. Jago, Seattle, both of WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/693,059

(22) Filed: Oct. 20, 2000

(51) Int. Cl.[7] ................................................ A61B 8/00
(52) U.S. Cl. ....................................................... 600/443
(58) Field of Search ................................ 600/447, 448, 600/449, 443, 300; 367/11

(56) References Cited

U.S. PATENT DOCUMENTS

| | | |
|---|---|---|
| 4,887,306 A | 12/1989 | Hwang et al. |
| 5,197,477 A | 3/1993 | Peterson et al. |
| 5,413,105 A | 5/1995 | Forestieri |
| 5,487,389 A | 1/1996 | Banjanin et al. |
| 5,623,929 A | 4/1997 | Weng |
| 5,706,819 A | 1/1998 | Hwang et al. |
| 5,782,769 A | 7/1998 | Hwang et al. |
| 5,833,613 A | 11/1998 | Averkiou et al. |
| 5,879,303 A | 3/1999 | Averkiou et al. |
| 5,910,118 A | 6/1999 | Kanda et al. |
| 5,924,980 A * | 7/1999 | Coetzee ........................ 600/300 |
| 5,951,478 A | 9/1999 | Hwang et al. |
| 5,980,459 A * | 11/1999 | Chiao et al. .................. 600/447 |
| 6,016,285 A * | 1/2000 | Wright et al. .................. 367/11 |
| 6,108,572 A * | 8/2000 | Panda et al. .................. 600/407 |
| 6,190,322 B1 * | 2/2001 | Clark ............................ 600/443 |
| 6,193,662 B1 * | 2/2001 | Hwang ......................... 600/447 |
| 6,228,031 B1 * | 5/2001 | Hwang et al. ................ 600/447 |
| 6,241,674 B1 * | 6/2001 | Phillips et al. ............... 600/443 |

* cited by examiner

*Primary Examiner*—Francis J. Jaworski
*Assistant Examiner*—Maulin Patel
(74) *Attorney, Agent, or Firm*—W. Brinton Yorks, Jr.

(57) ABSTRACT

Ultrasonic imaging apparatus and method are described for reducing the flash artifact in ultrasonic harmonic images. Harmonic signals are separated by pulse inversion separation which uses multiple transmit pulses which may be subject to motion artifacts. The motion artifacts are detected and subtracted from the harmonic signals to produce harmonic images with reduced flash artifacts. The motion artifacts may also be reduced by notch filtering. In another embodiment the amount of motion in the image is detected and the flash artifact is reduced in accordance with the detected motion. The amount of artifact signal which is removed is variable in accordance with anticipated image motion or clinical application.

30 Claims, 4 Drawing Sheets

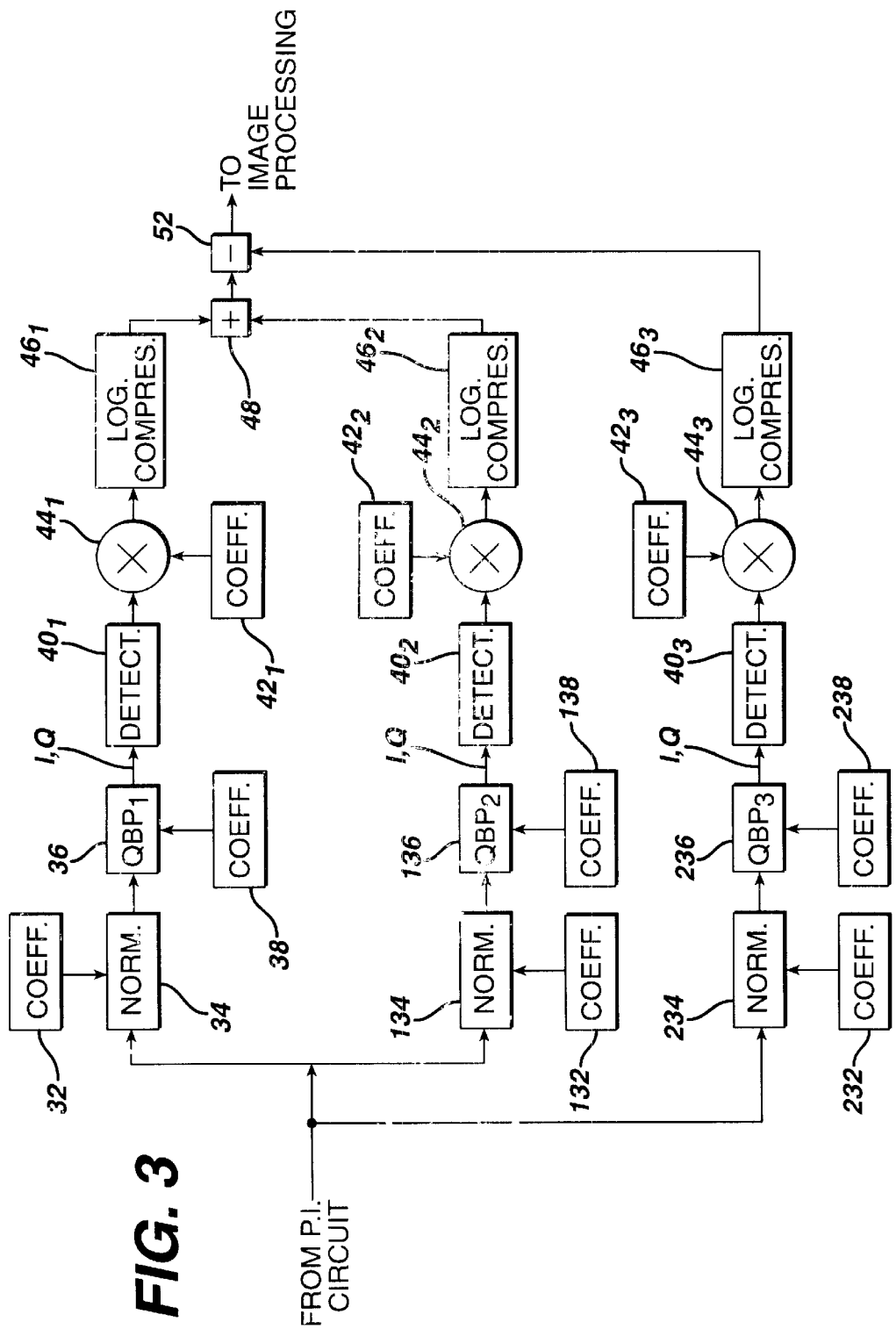

ULTRASONIC HARMONIC FLASH SUPPRESSION

This invention relates to ultrasonic harmonic imaging systems and, in particular, to the elimination of flash artifacts from ultrasonic harmonic images.

Ultrasonic imaging systems can now produce diagnostic images using the higher harmonics of the fundamental transmit frequency. Harmonic components in echo signals can arise from two sources: harmonic contrast agents and tissue harmonic distortion. Examples of imaging techniques utilizing these harmonic sources can be found in U.S. Pat. Nos. 5,833,613 and 5,879,303. In both cases the received echoes will contain both large amplitude fundamental frequency signal components and relatively lower amplitude harmonic (nonlinear) components. Consequently, when it is desired to produce an image using only the harmonic components, a method must be employed to separate the harmonic and fundamental frequency components of the echo signal.

Two approaches have been used to separate these components. One is to filter the echo signal so as to pass the harmonic components while attenuating the fundamental components. A high pass or band pass filter can perform this function. The other approach is a multi-pulse signal processing technique known as pulse inversion. Pulse inversion harmonic separation was originally developed for imaging ultrasound contrast agents, but is equally applicable when imaging tissue in the absence of contrast agents. See, for instance, U.S. Pat. Nos. 5,706,819 and 5,951,478. Pulse inversion is a multiple transmit pulse scheme whereby two or more pulses of differently modulated phase, amplitude, and/or polarity are successively transmitted to the same target. Preferably the transmitted pulses are of opposite phase or polarity. The received r.f. echoes from the differently modulated pulses are then summed. In a perfectly stationary target, this summation causes total cancellation of the fundamental signal, resulting in a purely second harmonic signal arising from the non-linearities in the target. In some cases, images of tissue made using pulse inversion harmonic imaging are preferred over conventional (i.e. single pulse) harmonic imaging because of improved speckle suppression and better spatial resolution.

However, when tissue motion occurs between the times that the two pulses are transmitted, incomplete cancellation of the fundamental signal occurs. Since the fundamental component in an echo signal is typically 30 dB larger than the second harmonic component, imperfect cancellation results in a high amplitude fundamental signal dominating the second harmonic signal in scanlines transmitted through sections of moving tissue. In a two dimensional pulse inversion image, the motion induced fundamental component presents itself as a bright flashing of the image in regions where tissue motion occurs, or while the scanhead is moved around in real-time scanning. This flash artifact is rather distracting and is particularly a problem in obstetrics where the fetus is often moving. This artifact is also a problem in abdominal imaging when breathing motion and movement of the scanhead in searching for the desired structures causes this rapid variation in image brightness.

Various approaches have been presented in an effort to eliminate this motion-induced flash artifact. One method involves using a transmit pulse scheme of more than two pulses to better reject the fundamental received echoes from a moving targets. See D. Hope Simpson, C. T. Chin, and P. N. Burns, "Pulse Inversion Doppler: A New Method for Detecting Nonlinear Echoes from Microbubble Contrast Agents" *IEEE Trans. Ultrason. Ferrorelect., Freq. Contr.*, Vol. 46, No. 2, pp. 372–382 (1999). The disadvantage to such a multiple pulse scheme is a further reduction in frame rate. If, for instance, three pulses are transmitted for each scanline direction, then the frame rate is concomitantly reduced by ⅔ compared to the standard dual-pulse pulse inversion harmonic image. Since pulse inversion harmonic imaging already reduces the frame rate by a factor of two relative to normal imaging, a further reduction in frame rate is not desirable, especially in abdominal and obstetrical imaging.

In accordance with the principles of the present invention, a method and apparatus are presented for eliminating this harmonic flash artifact. Two or more echo signals from a target are combined to separate harmonic signal components and flash artifacts resulting from relative motion between the tissue being imaged and the transducer. The present inventors have noted that the motion artifact is a large, relatively narrow band signal that occurs at the fundamental frequency. A bandpass or lowpass filter is employed to extract the artifact from the harmonic signal. The extracted artifact is then subtracted from the separated harmonic signal, leaving a harmonic signal substantially free of the motion artifact.

In the drawings:

FIG. 3 illustrates the speckle reduction and flash suppression portions of the ultrasound system of FIG. 2 in further detail.

Figure 1:
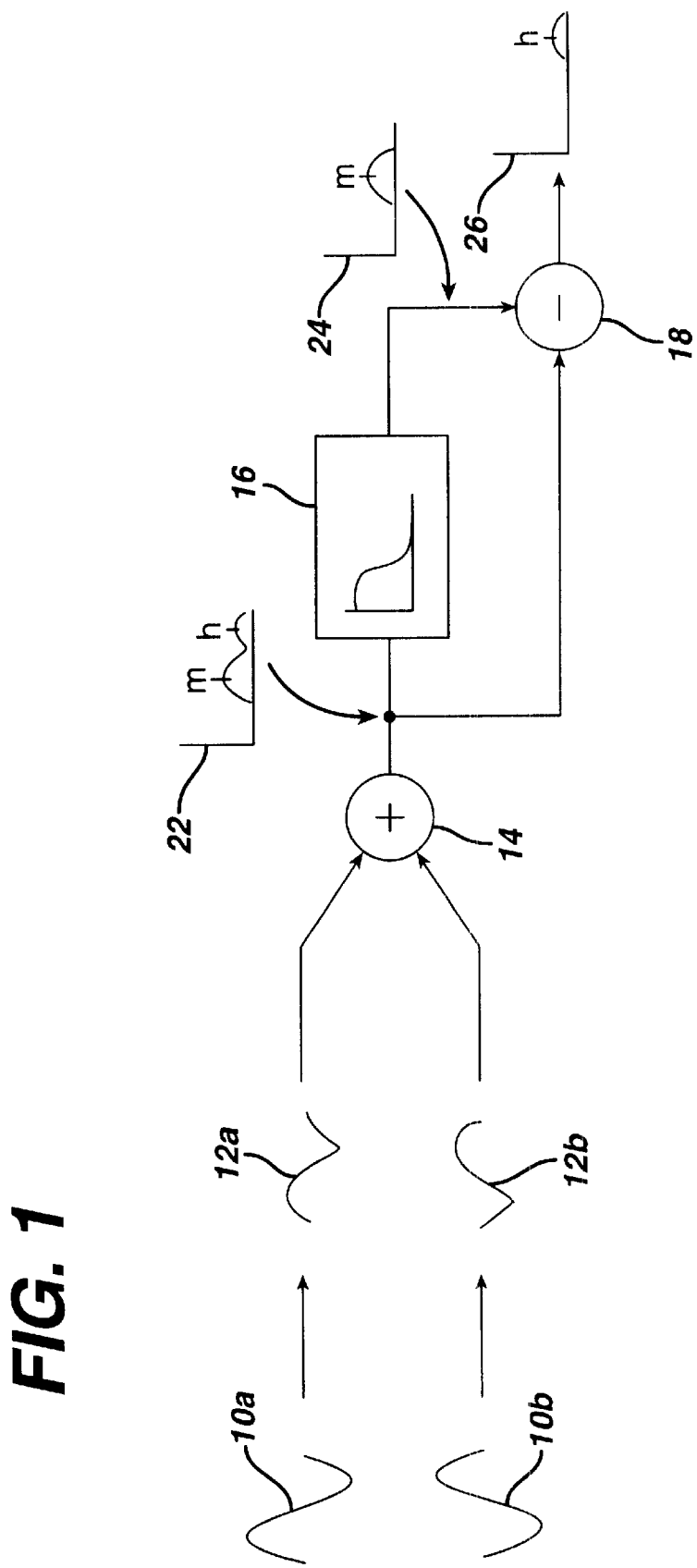
FIG. 1 is a flow diagram illustrating how the flash artifact may be eliminated from a harmonic signal in accordance with the principles of the present invention.

FIG. 1 illustrates two ultrasound pulses 10*a* and 10*b* which are successively transmitted to a target. The transmit pulses can be of different polarity, differently phase modulated, or of different amplitudes. In this example the two transmit pulses are of different phase and polarity; one is the inverse of the other. In response to each transmit pulse, the target returns an echo. Transmit pulse 10*a* returns an echo 12*a*, and transmit pulse 10*b* returns an echo 12*b*. These two echoes are combined by an adder 14. As a result of this combination, the fundamental frequency components, being linear, will be of opposing phase or polarity and will cancel. The second harmonic frequency components, being quadratic in nature, will reinforce each other. As a consequence the adder 14 produces a separated harmonic signal. If a subtractor is used instead of the adder, the harmonic components will cancel and the fundamental (linear) components will reinforce each other to produce separated fundamental frequency components.

When phase or polarity modulation is used, the fundamental signal cancellation results from the opposing phase or polarity of the nonlinear components. Pulse inversion separation using pulses which are both phase and amplitude modulated is described in U.S. Pat. No. 6,319,203, entitled "ULTRASONIC NONLINEAR IMAGING AT FUNDAMENTAL FREQUENCIES."

In the absence of relative scanhead motion, the harmonic signals produced by the adder 14 will be free of motion artifacts. But when motion is present between transmit pulses, the fundamental (linear) signal components will not completely cancel, leaving a residual motion-caused component in the fundamental frequency band, as shown by the peak "m" (motion) in the spectral plot 22 at the output of the adder 14, where "h" is the peak of the second harmonic signal band. In accordance with the principles of the present invention, the artifact-contaminated harmonic signal is filtered by a filter 16. The filter 16 may be a lowpass filter as illustrated which passes the artifact component to the exclusion of the desired harmonic component. The present inventors have found that a bandpass filter with a narrow passband centered at the fundamental frequency will perform well. The signal produced by the filter 16 is essentially the motion artifact as illustrated by the spectral plot 24 at the output of the filter. This artifact signal is then subtracted from the artifact-contaminated harmonic signal by a subtractor 18 to leave an artifact-reduced harmonic signal as shown by the spectral plot 26 at the output of the subtractor.

Figure 2:
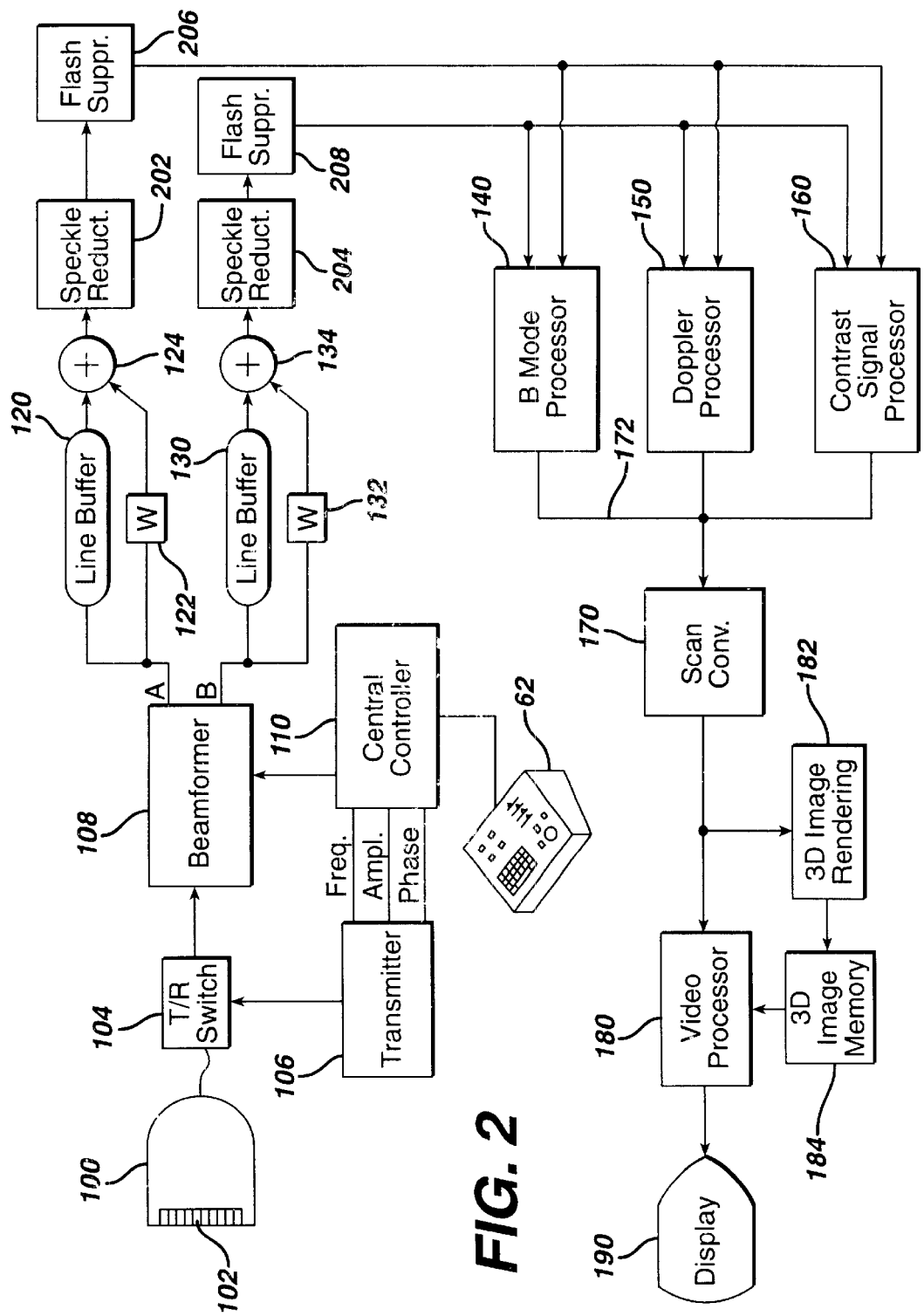
FIG. 2 illustrates in block diagram form an ultrasound system constructed in accordance with the principles of the present invention.

An ultrasound system constructed in accordance with the principles of the present invention is shown in FIG. 2. An ultrasound scanhead 100 including an array transducer 102 is connected to a transmit/receive (T/R) switch 104. A central controller 110 responsive to a user interface 62 sets the frequency, amplitude, and phase or polarity of the transmit pulses. A transmitter 106 transmits the pulses set by the central controller by way of the T/R switch, exciting elements of the transducer array in a timed sequence to transmit appropriately steered and focused beams. The echoes received by the transducer array 102 are coupled by the T/R switch to a receive beamformer 108. In this example the beamformer is shown as a multiline beamformer which, under control of the central controller, produces two spatially adjacent receive scanlines of coherent echo signals A and B. The echo sequences produced in response to the first transmit pulse are stored in line buffers 120 and 130 for the A and B multilines, respectively. The echo sequences produced in response to the second transmit pulse are weighted (when amplitude modulation is employed) by weighting circuits 122 and 132 to normalize the echo signals for the difference in transmit pulse amplitudes. After this normalization the previous and current echo sequences are combined in summers 124 and 134 respectively to separate the nonlinear (second harmonic) frequency components. When these summers are set for subtraction the linear (fundamental frequency) components will be emphasized for oppositely phased or poled transmit pulses. The separated fundamental or harmonic echo signals are then processed to reduce image speckle by speckle reduction circuits 202 and 204. Harmonic echo signals which may be contaminated by motion artifacts are enhanced by flash suppression circuits 206 and 208.

The echo signals may be processed by a B mode processor 140, a Doppler processor 150, and/or a contrast signal processor 160. The B mode processor will produce amplitude detected image signals of structure in the body, and the Doppler processor will process ensembles of echo signals to produce image signals of tissue or flow motion. The contrast signal processor is similar to the previous processors, generally with a threshold which separates contrast harmonic signals from tissue harmonic signals. Contrast agents can be displayed in either Doppler or B mode format. Image signals from the three processors are coupled over an image signal bus 172 to a scan converter 170, which interpolates the motion image signals and puts the scanlines in the desired image format. The image information can be applied to a video processor 180 for display of a two dimensional image on a display 190. The image information can also be formed into three dimensional presentations by 3D image rendering 182. Three dimensional images are stored in a 3D image memory 184 and displayed on the display 190 by way of the video processor 180.

A detailed embodiment of the speckle reduction circuits and the flash suppression circuits of FIG. 2 are shown in FIG. 3. This drawing illustrates the speckle reduction and flash suppression processing for one channel of the multiline receiver; the same processing can be used for the second or additional scanlines, or the scanlines can be processed by a fewer number of processors using time interleaved processing of multiple scanlines. In FIG. 3 the signal and data lines connecting the blocks of the block diagram all represent multi-conductor digital data paths, as the processor of the illustrated embodiment is entirely digital. Scanline echo data from a pulse inversion separator circuit is applied in parallel to the two processing channels, one beginning with normalization stage 34 and ending at the output of log compression processor $46_1$, and the other beginning with normalization stage 134 and ending at the output of log compression processor $46_2$. One of these processing channels is set as a high frequency channel and the other is set as a low frequency channel. Each channel has a normalization stage 34,134 which multiplies the scanline data by a scale factor on a sample by sample basis to produce gain or attenuation that can vary with the depth of the body from which each sample returned. The function of the normalization stages is two-fold. One is to compensate for a transducer aperture which expands with depth of scan. The second function is to equalize the nominal signal amplitudes of the two channels to account for disparities such as depth dependent frequency attenuation. The scale factor for each channel is provided by normalization coefficients stored in or generated by coefficient circuits 32,132, which in a preferred embodiment are digital memories. As the multiplying coefficients are changed along the sequence of scanline echoes, depth dependent gain or attenuation is produced.

The normalized echo signals in each channel are coupled to quadrature bandpass filters (QBPs) in each channel. The quadrature bandpass filters provide three functions: band limiting the RF scanline data, producing in-phase and quadrature pairs of scanline data, and decimating the digital sample rate. Each QBP comprises two separate filters, one producing in-phase samples (I) and the other producing quadrature samples (Q), with each filter being formed by a plurality of multiplier-accumulators (MACs) implementing an FIR filter. The length of the filter is a product of the decimation rate and the number of MACs used to form the filter, which determine the number of incoming echo samples used to produce the accumulated output signal. The filter characteristic is determined by the values of the multiplying coefficients. Different sets of coefficients for different filter functions are stored in coefficient memories 38,138, which are coupled to apply selected coefficients to the multipliers of the MACs. The MACs effectively convolve the received echo signals with sine and cosine representative coefficients, producing output samples which are in a quadrature relationship. For bandpass filtering, the coefficients of the active QBPs additionally implement a low pass filter function that is frequency shifted to form, in combination with the sine (for I) and cosine (for Q) functions, a bandpass filter for the quadrature samples. In the instant example, $QBP_1$ in channel 30a is producing I and Q samples of the scanline data in a first, low frequency passband, and $QBP_2$ in channel 30b is producing I and Q samples of the scanline data in a second, higher frequency passband. Thus, the spectrum of the original broadband echo signals is divided into a high frequency band and a low frequency band. To complete the signal dropout and speckle reduction process, the echo data in the passband produced by $QBP_1$ of the first channel is detected by a detector $40_1$ and the detected signals are coupled to one input of a summer 48. In a preferred embodiment detection is performed digitally by implementing the algorithm $(I^2+Q^2)^2$. The echo data in the second channel produced by $QBP_2$ is detected by a detector 402 and these detected signals are coupled to a second input of the summer 48. When the signals of the two passbands are combined by the summer 48, the decorrelated signal dropout and speckle effects of the two passbands will at least partially cancel, reducing the signal dropout and speckle artifacts in the image created from the signals.

Following the detector in each channel is a gain stage formed by multipliers $44_1, 44_2$ which receive weighting coefficients from coefficient memories $42_1, 42_2$. The purpose of this gain stage is to partition the balance of analog and digital gains in the ultrasound system for optimal system performance. Some of the gains in the echo signal path may be automatically implemented by the ultrasound system, while others, such as manual gain control and TGC gain, may be controlled by the user. The system partitions these gains so that the analog gains preceding the ADCs (analog to digital converters) of the beamformer are adjusted optimally for the dynamic input range of the ADCs. The digital gain is adjusted to optimize the brightness of the image. The two gains together implement gain control changes effected by the user. In the preferred embodiment the gain imparted to the scanline signals by the multipliers $44_1, 44_2$ is selected in concert with the gain of the preceding normalization stage 34,134 in the channel.

The signals produced by the gain stages $44_1, 44_2$ generally exhibit a greater dynamic range than may be accommodated by the display 50. Consequently, the scanline signals of the multipliers are compressed to a suitable dynamic range by lookup tables. Generally the compression is logarithmic, as indicated by log compression processors $46_1, 46_2$. The output of each lookup table is proportional to the log of the signal input value. These lookup tables are programmable so as to provide the ability to vary the compression curves, and the brightness and dynamic range of the scanline signals sent on for display. The dropout and speckle reduced signals at the output of the summer 48 are coupled to one input of a subtractor 52. Further details of these two processing channels may be found in U.S. Pat. No. 5,879,303.

In accordance with the principles of the present invention a third processing channel is responsive to the separated echo signals to detect motion artifacts of the harmonic signals by filtering. The normalization stage 234, the detector $40_3$, the gain stage $42_3, 44_3$, and the log compression processor $46_3$ operate in a similar manner to their complementary components in the first two channels. The $QBP_3$ also operates in a similar manner as the other QBPs, but at a lower passband frequency. The $QBP_3$ is set to the frequency of the motion artifact signals which are to be removed from the harmonic signals, which in a preferred embodiment is around the nominal center frequency of the fundamental transmit signal band. The amplitude of the detected motion artifact signals is set to a desired level by selection of the coefficients of either the normalization stage 234 or the gain stage $42_3, 44_3$. The detected motion artifact signals are applied to one input of a subtractor 52, which subtracts the artifact signals from the speckle and dropout reduced harmonic signals produced by the summer 48. The harmonic signals are then coupled to the processors 140, 150,160 for image processing and display.

Figure 4A:
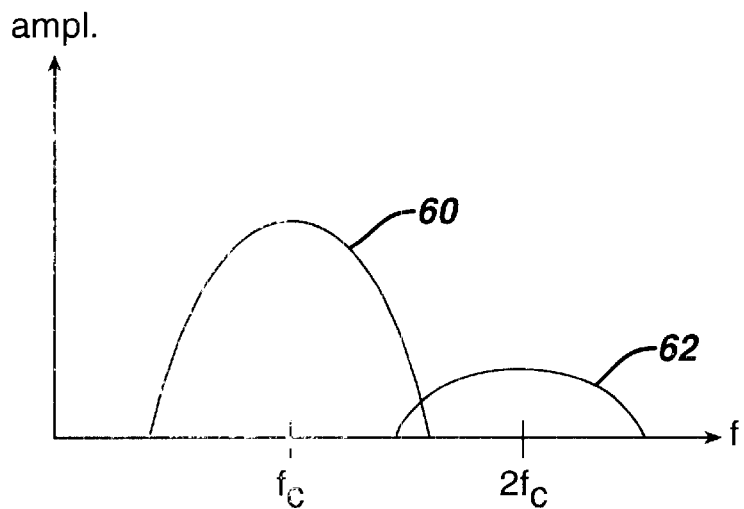
FIGS. 4*a* and 4*b* illustrate exemplary passbands of the apparatus of FIG. 3.
Figure 4B:
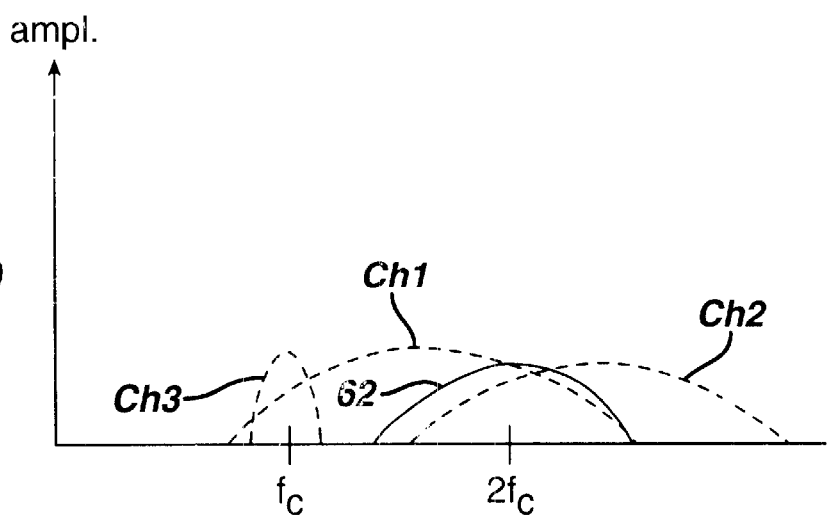

Exemplary passbands of the three processing channels of FIG. 3 are shown in FIGS. 4a and 4b. FIG. 4a shows a fundamental frequency transmit band 60, centered about a nominal center frequency $f_c$. In a preferred embodiment a broadband transmit signal is used to provide better resolution and image quality. The use of a broad transmit band 60 means that some of the harmonic components of the lower fundamental signals can overlap the fundamental frequency echo band as shown by the harmonic received band 62, which is centered about a nominal center frequency $2f_c$ and overlaps the transmit (fundamental echo) band 60 at the lower end of the receive band 62.

FIG. 4b illustrates exemplary QBP passband which may be implemented for the transmit and receive bands of FIG. 4a. The two bands denoted Ch1 and Ch2 are the passbands formed by $QBP_1$ and $QBP_2$ of the first two processing channels of FIG. 3. For frequency compounding speckle reduction it is usually desirable to separate the received signals into two or more non-overlapping bands for best band-to-band decorrelation of the speckle characteristics of the passband signals. However the present inventors have chosen to utilize partially overlapping passbands Ch1 and Ch2, which correspond to upper and lower frequency components of the second harmonic signal. The Ch1 band, being a broad band filter, will see any residual fundamental energy caused by noncancellation of the fundamental due to motional effects. In accordance with the present invention the third channel has a passband Ch3 which, like the fundamental signal band, is centered about the nominal center frequency $f_c$. The present inventors have found that motion artifacts have frequencies predominately located in the vicinity of the center of the fundamental band, and therefore use of this narrow passband Ch3 will detect the motion artifacts which can then be subtracted from the signals of the combined Ch1 and Ch2 passbands to eliminate the flash artifact. In a preferred embodiment the gain of the third channel is set differently for different applications in consideration of the amount of motion artifacts that might be expected. Where minimal motion is to be expected, such as when scanning the abdomen, the motion artifact signals will be weighted relatively low so that a small amount of signal energy is subtracted from the desired signal band. When significant motion artifacts are to be expected, such as when imaging the heart, the detected motion artifact signals will be more greatly weighted (more gain) to cancel more anticipated motion artifacts. In an intermediate case, such as imaging the carotid artery where some pulsatile motion is to be expected, the motion artifacts to be subtracted will be moderately weighted.

Use of the passbands of FIG. 3 will provide a further benefit in the form of enhancement of the edges of structure in the harmonic image. That is due to the removal of some of the low frequency components by the artifact removal process, providing a relatively greater proportion of high frequency components to the image display.

One skilled in the art will recognize that the effect realized with the filters of FIG. 4b may be obtained with other filter combinations. For example, instead of subtracting the detected motion artifact components from the desired signals, a notch filter could be employed with the notch located at $f_c$ to notch out artifact components at that frequency. The depth of the notch is controlled to provide the desired degree of artifact reduction, which can be application-dependent as described above. The degree of artifact reduction can also be controlled by measuring the amount of motion in the image and using the detected motion as a control variable by, for instance, detecting motion in the image by frame to frame correlation. When a greater amount of motion is detected, as indicated by relatively low frame-to-frame correlation, a greater degree of artifact signal is removed, and a lesser degree is removed when little or no motion is detected in the image, which would be evidenced by relatively high frame to frame correlation. Motion can also be detected by integrating the energy out of the $QBP_3$ channel. One could also detect motion by receiving the two echoes used for a 2-pulse embodiment of pulse inversion processing, inverting one echo signal so that the echoes are of the same polarity, then correlating the echoes in the r.f. domain. The time shift associated with the peak of the correlation coefficient is a measure of motion and hence flash. The flash artifact can then be eliminated by shifting one of the waveforms by this time shift to time-align the two echoes prior to combining them for harmonic separation.

What is claimed is:

1. An ultrasonic diagnostic imaging system which produces harmonic images with reduced motional artifacts comprising:

a transducer which transmits fundamental frequency signals and receives echo signals in response thereto at a harmonic frequency;

a harmonic signal separator circuit which separates the harmonic signal components of the received echo signals;

an image display, responsive to the harmonic components, which produces a harmonic ultrasonic image;

a motion detection circuit which detects motion signal components in the received echo signals; and a motion artifact cancellation circuit, responsive to the motion detection circuit and coupled to the image display, which reduces motion artifacts in the harmonic ultrasonic image.

2. The ultrasonic diagnostic imaging system of claim 1, wherein the harmonic signal separator circuit comprises a pulse inversion processing circuit.

3. The ultrasonic diagnostic imaging system of claim 1, wherein the motion detection circuit comprises a filter circuit.

4. The ultrasonic diagnostic imaging system of claim 3, wherein the transmitted fundamental frequency signals exhibit a nominal center fundamental frequency, and wherein the filter is set to detect signals in the vicinity of the nominal center fundamental frequency.

5. The ultrasonic diagnostic imaging system of claim 3, wherein the motion detection circuit is responsive to separated harmonic signal components of the received echo signal which may be contaminated by motion artifacts.

6. The ultrasonic diagnostic imaging system of claim 5, wherein the motion artifact cancellation circuit comprises a subtractor which subtracts motion signal components from harmonic signal components which may be contaminated by motion artifacts.

7. The ultrasonic diagnostic imaging system of claim 5, wherein the motion artifact cancellation circuit comprises a notch filter which is set to remove signal components at an artifact signal frequency.

8. The ultrasonic diagnostic imaging system of claim 7, wherein the transmitted fundamental frequency signals exhibit a nominal center fundamental frequency, and wherein the notch filter is set to remove signal components in the vicinity of the nominal center fundamental frequency.

9. The ultrasonic diagnostic imaging system of claim 1, further comprising a speckle reduction circuit, responsive to separated harmonic signal components of the received echo signal which may be contaminated by motion artifacts, which reduces the speckle content of harmonic signal components.

10. The ultrasonic diagnostic imaging system of claim 9, wherein the speckle reduction circuit reduces the speckle content of harmonic signal components by frequency compounding.

11. The ultrasonic diagnostic imaging system of claim 10, wherein the speckle reduction circuit compounds bands of detected harmonic frequency signals.

12. A method for reducing motion artifacts from an ultrasonic harmonic image comprising:

transmitting a fundamental frequency transmit signal;

receiving echo signals at a harmonic of the fundamental frequency, which echo signals may also be contaminated by motion artifacts;

detecting motion artifacts in the received echo signals; and utilizing the detected motion artifacts to reduce motion artifacts in a displayed harmonic image.

13. The method of claim 12, further comprising separating harmonic signals from the received echo signals, which separated harmonic signals may be contaminated by motion artifacts.

14. The method of claim 13, wherein separating comprises separating harmonic signals from the received echo signals by pulse inversion.

15. The method of claim 14, wherein detecting comprises filtering pulse inversion separated harmonic signals at a motion artifact signal frequency.

16. The method of claim 15, wherein the transmit signal exhibits a nominal fundamental frequency; and wherein filtering comprises filtering pulse inversion separated harmonic signals in the vicinity of the nominal fundamental frequency.

17. The method of claim 16, wherein utilizing comprises subtracting filtered received signals from the pulse inversion separated harmonic echo signals.

18. The method of claim 17, wherein utilizing comprises subtracting filtered pulse inversion separated harmonic signals of a predetermined amplitude from the pulse inversion separated harmonic echo signals, wherein the predetermined amplitude is determined by the amount of anticipated motion in the image.

19. The method of claim 18, wherein the predetermined amplitude is determined by the application for which the imaging is being performed.

20. A method for reducing motion artifacts from an ultrasonic harmonic image comprising:

transmitting a fundamental frequency transmit signal;

receiving echo signals at a harmonic of the fundamental frequency, which echo signals may also be contaminated by motion artifacts;

detecting the presence of motion in the received echo signals; and utilizing the detection of motion to reduce motion artifacts a displayed harmonic image.

21. The method of claim 20, wherein reducing motion artifacts is performed by notch filtering.

22. The method of claim 21, wherein the transmit signal exhibits a nominal fundamental frequency; and wherein notch filtering is performed on pulse inversion separated harmonic echo signals in the vicinity of the nominal fundamental frequency.

23. A method for reducing motion artifacts from an ultrasonic harmonic image comprising:

transmitting a fundamental frequency transmit signal;

receiving echo signals at the fundamental frequency and at a harmonic of the fundamental frequency, which echo signals may also be contaminated by motion artifacts;

separating harmonic signals of the echo signals by pulse inversion;

detecting motion artifacts in the separated harmonic signals;

removing motion artifacts from the separated harmonic signals; and producing an ultrasonic harmonic image using the separated harmonic signals from which motion artifacts have been removed.

24. The method of claim 23, wherein removing motion artifacts is performed by subtraction.

25. The method of claim 24, wherein amplitude-variable motion artifacts are subtracted from the harmonic signals, wherein the amplitude is variable in accordance with the anticipated amount of motion in the region being imaged.

26. The method of claim 25, wherein the amplitude is variable in accordance with the clinical application in which the method is being used.

27. The method of claim 23, wherein removing motion artifacts is performed by notch filtering.

28. The method of claim 23, further comprising reducing the speckle content of the ultrasonic harmonic image.

29. The method of claim 28, wherein reducing the speckle content is done by frequency compounding.

30. The method of claim 25, wherein detecting motion artifacts comprises detecting the degree of motion contamination of the received echo signals, and wherein the amplitude is variable in accordance with the degree of motion contamination detected.

* * * * *